United States Patent
Fang et al.

(10) Patent No.: US 7,166,725 B2
(45) Date of Patent: Jan. 23, 2007

(54) BENZO[D]ISOXAZOL-3-OL DAAO INHIBITORS

(75) Inventors: Q Kevin Fang, Wellesley, MA (US); Seth Hopkins, Clinton, MA (US); Michele Heffernan, Worcester, MA (US); Milan Chytil, Clinton, MA (US); Peter Wipf, Pittsburgh, PA (US)

(73) Assignee: Sepracor Inc., Marlborough, MA (US)

( * ) Notice: Subject to any disclaimer, the term of this patent is extended or adjusted under 35 U.S.C. 154(b) by 149 days.

(21) Appl. No.: 11/024,151

(22) Filed: Dec. 28, 2004

(65) Prior Publication Data

US 2005/0143434 A1  Jun. 30, 2005

Related U.S. Application Data

(60) Provisional application No. 60/532,978, filed on Dec. 29, 2003.

(51) Int. Cl.
*C07D 261/20* (2006.01)
*A61K 31/42* (2006.01)

(52) U.S. Cl. .................... 548/241; 514/379
(58) Field of Classification Search ............... 548/241
See application file for complete search history.

(56) References Cited

U.S. PATENT DOCUMENTS

| 4,738,709 | A | 4/1988 | Nielsen ........................ 71/94 |
| 5,523,278 | A | 6/1996 | Wepplo ...................... 504/271 |
| 5,578,627 | A | 11/1996 | Takeda et al. .............. 514/379 |
| 5,620,997 | A | 4/1997 | Bolton et al. |
| 5,668,162 | A | 9/1997 | Domagala et al. |
| 6,096,771 | A | 8/2000 | Kojima et al. ............. 514/379 |

FOREIGN PATENT DOCUMENTS

| EP | 0 101 786 | | 3/1984 |
| EP | 1 262 181 | A | 12/2002 |
| JP | 04 077476 | | 3/1992 |
| WO | WO 2005/089753 | | 9/2005 |

OTHER PUBLICATIONS

Slawik, T and Kowalsky, C., "Lipophilicity of a series of 1,2 benzisothizol-3(2H)-ones determined by reverse-phase thin-layer chromatography" *J. Chromatography A* 952, 295-299 (2002).

Fischer, et al. "On Benzisothiazolones: A Series with a Wide Range of Bacteriostatic and Fungistatic Activity" *J. Chem. Soc.* 1301-1306 (1923).

Inukai, et al., "ortho-Disubstituted F-Benzenes. III. Preparation of (F-Benzo)heterocyclic Compounds from F-Benzoic Acid and F-Phenol, and the Reactions of Some Intermediary F-Benzoyl-and F-Phenoxy Compounds," *Bull. Chem. Soc.*, Jpn. 54, 3447-3452 (1981).

Primary Examiner—Kamal A. Saeed
Assistant Examiner—Nyeemah Grazier
(74) *Attorney, Agent, or Firm*—Heslin Rothenberg Farley & Mesiti P.C.

(57) ABSTRACT

Methods for increasing D-Serine concentration and reducing concentration of the toxic products of D-Serine oxidation, for enhancing learning, memory and/or cognition, or for treating schizophrenia, Alzheimer's disease, ataxia, or neuropathic pain, or preventing loss in neuronal function characteristic of neurodegenerative diseases involve administering to a subject in need of treatment a therapeutic amount of a compound of formula I, or a pharmaceutically acceptable salt or solvate thereof:

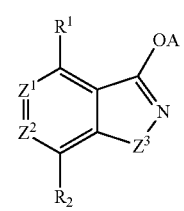

wherein
$Z^1$ is N or $CR^3$;
$Z^2$ is N or $CR^4$;
$Z^3$ is O or S;
A is hydrogen, alkyl or $M^+$;
M is aluminum, calcium, lithium, magnesium, potassium, sodium, zinc or a mixture thereof;
$R^1$, $R^2$, $R^3$ and $R^4$ are independently selected from hydrogen, alkyl, hydroxy alkoxy, aryl, acyl, halo, cyano, haloalkyl, $NHCOOR^5$ and $SO_2NH_2$;
$R^5$ is aryl, arylalkyl, heteroaryl or heteroarylalkyl;
at least one of $R^1$, $R^2$, $R^3$ and $R^4$ is other than hydrogen; and
at least one of $Z^1$ and $Z^2$ is other than N.

3 Claims, No Drawings

BENZO[D]ISOXAZOL-3-OL DAAO INHIBITORS

CROSS-REFERENCE TO RELATED APPLICATIONS

This application is a non-provisional of and claims the benefit of U.S. Provisional Application No. 60/532,978, filed Dec. 29, 2003. The entire disclosure of U.S. Provisional Application No. 60/532,978 is incorporated herein by reference.

BACKGROUND OF THE INVENTION

The enzyme D-amino acid oxidase (DAAO) metabolizes D-amino acids, and in particular, metabolizes D-serine in vitro at physiological pH. DAAO is expressed in the mammalian brain and periphery. D-Serine's role as a neurotransmitter is important in the activation of the N-methyl-D-aspartate (NMDA) selective subtype of the glutamate receptor, an ion channel expressed in neurons, here denoted as NMDA receptor. Small organic molecules, which inhibit the enzymatic cycle of DAAO, may control the levels of D-serine, and thus influence the activity of the NMDA receptor in the brain. NMDA receptor activity is important in a variety of disease states, such as schizophrenia, psychosis, ataxias, ischemia, several forms of pain including neuropathic pain, and deficits in memory and cognition.

Small organic molecules that inhibit the enzymatic cycle of DAAO may also control production of toxic metabolites of D-serine oxidation, such as hydrogen peroxide and ammonia. Thus, these molecules may influence the progression of cell loss in neurodegenerative disorders. Neurodegenerative diseases are diseases in which CNS neurons and/or peripheral neurons undergo a progressive loss of function, usually accompanied by (and perhaps caused by) a physical deterioration of the structure of either the neuron itself or its interface with other neurons. Such conditions include Parkinson's disease, Alzheimer's disease, Huntington's disease and neuropathic pain. N-methyl-D-aspartate (NMDA)-glutamate receptors are expressed at excitatory synapses throughout the central nervous system (CNS). These receptors mediate a wide range of brain processes, including synaptic plasticity, that are associated with certain types of memory formation and learning. NMDA-glutamate receptors require binding of two agonists to effect neurotransmission. One of these agonists is the excitatory amino acid L-glutamate, while the second agonist, at the so-called "strychnine-insensitive glycine site", is now thought to be D-serine. In animals, D-serine is synthesized from L-serine by serine racemase and degraded to its corresponding ketoacid by DAAO. Together, serine racemase and DAAO are thought to play a crucial role in modulating NMDA neurotransmission by regulating CNS concentrations of D-serine.

Alzheimer's disease is manifested as a form of dementia that typically involves mental deterioration, reflected in memory loss, confusion, and disorientation. In the context of the present invention, dementia is defined as a syndrome of progressive decline in multiple domains of cognitive function, eventually leading to an inability to maintain normal social and/or occupational performance. Early symptoms include memory lapses and mild but progressive deterioration of specific cognitive functions, such as language (aphasia), motor skills (apraxia) and perception (agnosia). The earliest manifestation of Alzheimer's disease is often memory impairment, which is required for a diagnosis of dementia in both the National Institute of Neurological and Communicative Disorders and Stroke-Alzheimer's Disease- and the Alzheimer's Disease and Related Disorders Association (NINCDS-ADRDA) criteria (McKhann et al., 1984, Neurology 34:939–944), which are specific for Alzheimer's disease, and the American Psychiatric Association's Diagnostic and Statistical Manual of Mental Disorders, Fourth Edition (DSM-IV) criteria, which are applicable for all forms of dementia. The cognitive function of a patient may also be assessed by the Alzheimer's disease Assessment Scale-cognitive subscale (ADAS-cog; Rosen et al., 1984, Am. J. Psychiatry 141:1356–1364). Alzheimer's disease is typically treated by acetylcholine esterase inhibitors such as tacrine hydrochloride or donepezil. Unfortunately, the few forms of treatment for memory loss and impaired learning available at present are not considered effective enough to make any significant difference to a patient, and there is currently a lack of a standard nootropic drug for use in such treatment.

Neuropsychiatric disorders include schizophrenia, autism, and attention deficit disorder. Clinicians recognize a distinction among such disorders, and there are many schemes for categorizing them. The *Diagnostic and Statistical Manual of Mental Disorders, Revised*, Fourth Ed., (DSM-IV-R), published by the American Psychiatric Association, provides a standard diagnostic system upon which persons of skill rely, and is incorporated herein by reference. According to the framework of the DSM-IV, the mental disorders of Axis I include: disorders diagnosed in childhood (such as Attention Deficit Disorder (ADD) and Attention Deficit-Hyperactivity Disorder (ADHD)) and disorders diagnosed in adulthood. The disorders diagnosed in adulthood include (1) schizophrenia and psychotic disorders; (2) cognitive disorders; (3) mood disorders; (4) anxiety related disorders; (5) eating disorders; (6) substance related disorders; (7) personality disorders; and (8) "disorders not yet included" in the scheme.

ADD and ADHD are disorders that are most prevalent in children and are associated with increased motor activity and a decreased attention span. These disorders are commonly treated by administration of psychostimulants such as methylphenidate and dextroamphetamine sulfate.

Schizophrenia represents a group of neuropsychiatric disorders characterized by dysfunctions of the thinking process, such as delusions, hallucinations, and extensive withdrawal of the patient's interests from other people. Approximately one percent of the worldwide population is afflicted with schizophrenia, and this disorder is accompanied by high morbidity and mortality rates. So called negative symptoms of schizophrenia include affect blunting, anergia, alogia and social withdrawal, which can be measured using SANS (Andreasen, 1983, Scales for the Assessment of Negative Symptoms (SANS), Iowa City, Iowa). Positive symptoms of schizophrenia include delusion and hallucination, which can be measured using PANSS (Positive and Negative Syndrome Scale) (Kay et al., 1987, Schizophrenia Bulletin 13:261–276). Cognitive symptoms of schizophrenia include impairment in obtaining, organizing, and using intellectual knowledge which can be measured by the Positive and Negative Syndrome Scale-cognitive subscale (PANSS-cognitive subscale) (Lindenmayer et al., 1994, J. Nerv. Ment. Dis. 182:631–638) or with cognitive tasks such as the Wisconsin Card Sorting Test. Conventional antipsychotic drugs, which act on the dopamine $D_2$ receptor, can be used to treat the positive symptoms of schizophrenia, such as delusion and hallucination. In general, conventional antipsychotic drugs and atypical antipsychotic drugs, which act on the dopamine $D_2$ and $5HT_2$ serotonin receptor, are limited in their ability to treat cognitive deficits and negative symptoms such as affect blunting (i.e., lack of facial expressions), anergia, and social withdrawal.

Other conditions that are manifested as deficits in memory and learning include benign forgetfulness and closed head injury. Benign forgetfulness refers to a mild tendency to be unable to retrieve or recall information that was once registered, learned, and stored in memory (e.g., an inability to remember where one placed one's keys or parked one's car). Benign forgetfulness typically affects individuals after 40 years of age and can be recognized by standard assessment instruments such as the Wechsler Memory Scale. Closed head injury refers to a clinical condition after head injury or trauma. Such a condition, which is characterized by cognitive and memory impairment, can be diagnosed as "amnestic disorder due to a general medical condition" according to DSM-IV.

Known inhibitors of DAAO include benzoic acid, pyrrole-2-carboxylic acids, and indole-2-carboxylic acids, as described by Frisell, et al., *J. Biol. Chem.*, 223:75–83 (1956) and Parikh et al., *JACS*, 80:953 (1958). Indole derivatives and particularly certain indole-2-carboxylates have been described in the literature for treatment of neurodegenerative disease and neurotoxic injury. EP 396124 discloses indole-2-carboxylates and derivatives for treatment or management of neurotoxic injury resulting from a CNS disorder or traumatic event or in treatment or management of a neurodegenerative disease. Several examples of traumatic events that may result in neurotoxic injury are given, including hypoxia, anoxia, ischemia, associated with perinatal asphyxia, cardiac arrest or stroke. Neurodegeneration is associated with CNS disorders such as convulsions and epilepsy. U.S. Pat. Nos. 5,373,018; 5,374,649; 5,686,461; 5,962,496 and 6,100,289, to Cugola, disclose treatment of neurotoxic injury and neurodegenerative disease using indole derivatives. None of the above references mention improvement or enhancement of learning, memory or cognition.

WO 03/039540 discloses enhancement of learning, memory and cognition and treatment of neurodegenerative disorders using DAAO inhibitors, including indole-2-carboxylic acids. However, there remains a need for new drugs which are clinically effective in treating memory defects, impaired learning and loss of cognition, and other symptoms related to NMDA receptor activity, or lack thereof.

SUMMARY OF THE INVENTION

It has been unexpectedly discovered that certain benzo[d]isoxazol-3-ol derivatives exhibit more potent inhibition of DAAO activity than known inhibitors. Dramatically low concentrations of these compounds have been observed to inhibit DAAO in vitro, particularly relative to known DAAO inhibitors such as benzoic acid, pyrrole-2-carboxylic acid, and indole-2-carboxylic acid. Because of this ability to inhibit DAAO activity, the certain benzisoxazole derivatives are useful in treating a variety of diseases and/or conditions wherein modulation of D-Serine levels, and/or its oxidative products, is effective in ameliorating symptoms, along with a reduction in undesirable side effects. In particular, the compounds may be useful for increasing D-Serine levels and reducing levels of toxic products of D-Serine oxidation; thus, the compounds are useful for enhancing learning, memory and/or cognition, or for treating schizophrenia, for treating or preventing loss of memory and/or cognition associated with Alzheimer's disease, for treating ataxia, or for preventing loss of neuronal function characteristic of neurodegenerative diseases.

Accordingly, in one aspect, the invention relates to methods for increasing D-Serine and reducing the toxic products of D-Serine oxidation, for enhancing learning, memory and/or cognition, or for treating schizophrenia, for treating or preventing loss of memory and/or cognition associated with Alzheimer's disease, for treating ataxia, or for preventing loss of neuronal function characteristic of neurodegenerative diseases.

The methods involve administering to a subject in need thereof a therapeutic amount of a compound of formula I, or a pharmaceutically acceptable salt or solvate thereof:

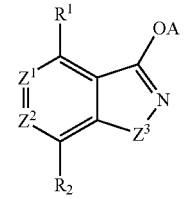

wherein
$Z^1$ is N or $CR^3$;
$Z^2$ is N or $CR^4$;
$Z^3$ is O or S;
A is hydrogen, alkyl or $M^+$;
M is aluminum, calcium, lithium, magnesium, potassium, sodium, zinc or a mixture thereof;
$R^1$, $R^2$, $R^3$ and $R^4$ are independently selected from hydrogen, alkyl, hydroxy alkoxy, aryl, acyl, halo, cyano, haloalkyl, $NHCOOR^5$ and $SO_2NH_2$;
$R^5$ is aryl, arylalkyl, heteroaryl or heteroarylalkyl; and
at least one of $Z^1$ and $Z^2$ is other than N.

In a second aspect the invention relates to methods for treating autism, schizophrenia, Alzheimer's disease, ataxia or neurodegenerative diseases, comprising administering a therapeutically effective amount of the above D-amino acid oxidase (DAAO) inhibitor of formula I to a subject in need of treatment for one or more of these conditions.

In preferred embodiments, the compounds of formula I are substituted benzo[d]isoxazol-3-ols, that is, at least one of $R^1$, $R^2$, $R^3$ and $R^4$ is other than hydrogen. Exemplary compounds are:

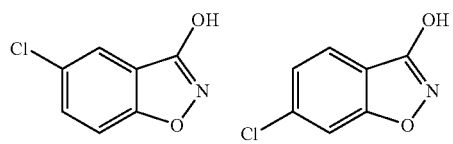

DETAILED DESCRIPTION OF THE INVENTION

The present invention relates to methods for increasing D-serine and reducing the toxic products of D-serine oxidation, for enhancing learning, memory and/or cognition, or for treating schizophrenia, for treating or preventing loss of memory and/or cognition associated with Alzheimer's disease, for treating ataxia, or for preventing loss of neuronal function characteristic of neurodegenerative diseases. The methods include administering to a subject a therapeutic amount of a compound of formula I:

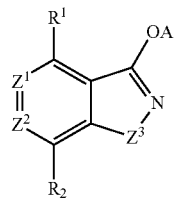

I or a pharmaceutically acceptable salt or solvate thereof.

wherein
$Z^1$ is N or $CR^3$;
$Z^2$ is N or $CR^4$;
$Z^3$ is O or S;
A is hydrogen, alkyl or $M^+$;
M is aluminum, calcium, lithium, magnesium, potassium, sodium, zinc or a mixture thereof;
$R^1$, $R^2$, $R^3$ and $R^4$ are independently selected from hydrogen, alkyl, hydroxy alkoxy, aryl, acyl, halo, cyano, haloalkyl, $NHCOOR^5$ and $SO_2NH_2$;
$R^5$ is aryl, arylalkyl, heteroaryl or heteroarylalkyl; and
at least one of $Z^1$ and $Z^2$ is other than N.

Therapeutic treatment with a compound of formula I improves and/or enhances memory, learning and cognition, particularly in individuals suffering from neurodegenerative diseases such as Alzheimer's, Huntington's or Parkinson's diseases. The compounds also ameliorate cognitive dysfunctions associated with aging and improve catatonic schizophrenia.

Compounds of formula I possess unique pharmacological characteristics with respect to inhibition of DAAO, and influence the activity of the NMDA receptor in the brain, particularly by controlling the levels of D-serine. Therefore, these compounds are effective in treating conditions and disorders, especially CNS-related disorders, modulated by DAAO, D-serine and/or NMDA receptor activity, with diminished side effects compared to administration of the current standards of treatment. These conditions and disorders include, but are not limited to, neuropsychiatric disorders, such as schizophrenia, autism, attention deficit disorder (ADD and ADHD) and childhood learning disorders, and neurodegenerative diseases and disorders, such as MLS (cerebellar ataxia), Alzheimer's disease, Parkinson's disease, Huntington's disease, amyotrophic lateral sclerosis, Down syndrome, neuropathic pain, multi-infarct dementia, status epilecticus, contusive injuries (e.g. spinal cord injury and head injury), viral infection induced neurodegeneration, (e.g. AIDS, encephalopathies), epilepsy, benign forgetfulness, and closed head injury. Compounds of formula I may also be useful for the treatment of neurotoxic injury which follows cerebral stroke, thromboembolic stroke, hemorrhagic stroke, cerebral ischemia, cerebral vasospasm, hypoglycemia, amnesia, hypoxia, anoxia, perinatal asphyxia and cardiac arrest.

Compounds of formula I are typically more selective than known DAAO inhibitors, including indole-2-carboxylates, and demonstrate higher selectivity for DAAO inhibition relative to binding at the NMDA receptor's D-serine binding site. The compounds also exhibit an advantageous profile of activity including good bioavailability. Accordingly, they offer advantages over many art-known methods for treating disorders modulated by DAAO, D-serine or NMDA receptor activity. For example, unlike many conventional antipsychotic therapeutics, DAAO inhibitors can produce a desirable reduction in the cognitive symptoms of schizophrenia. Conventional antipsychotics often produce undesirable side effects, including tardive dyskinesia (irreversible involuntary movement disorder), extra pyramidal symptoms, and akathesia, and these may be reduced or eliminated by administering compounds of formula I.

In another aspect, the present invention also relates to compounds of formula Ia, or pharmaceutically acceptable salts or solvates thereof, and pharmaceutical compositions containing them:

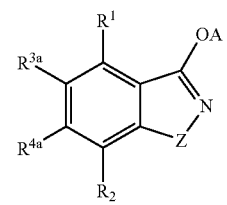

Ia wherein
A is hydrogen, alkyl or $M^+$;
M is aluminum, calcium, lithium, magnesium, potassium, sodium, zinc or a mixture therof;
Z is O or S;
$R^1$ and $R^2$ are independently selected from hydrogen, alkyl, hydroxy, alkoxy, aryl, acyl, halo, cyano, haloalkyl, $NHCOOR^5$ and $SO_2NH_2$;
$R^5$ is aryl, arylalkyl, eteroaryl or heteroarylalkyl; and
$R^{3a}$ and $R^{4a}$ are independently selected from alkyl, hydroxy, alkoxy, aryl, acyl, halo, cyano, haloalkyl, $NCOOR^5$ and $SO_2NH_2$.

Compounds of formula Ia form a subset of the compounds of formula I, and may therefore be used in the methods of the present invention. References herein to compounds of formula I is intended to include compounds of formula Ia.

In preferred embodiments, the compounds of formula I and Ia are benzo[d]isoxazol-3-ols, substituted at the 5-position and/or the 6-position. Preferred substituents for compounds of formula I and Ia and for 5-,6-and 5,6-substituted benzo[d]isoxazol-3-ols are halo, particularly chloro, hydroxy, alkyl, particularly higher alkyl ($C_6$–$C_{20}$) and alkoxy. Particularly preferred benzo[d]isoxazol-3-ols D-amino acid oxidase inhibitors include:

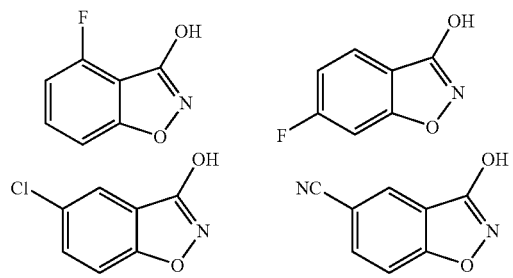

-continued

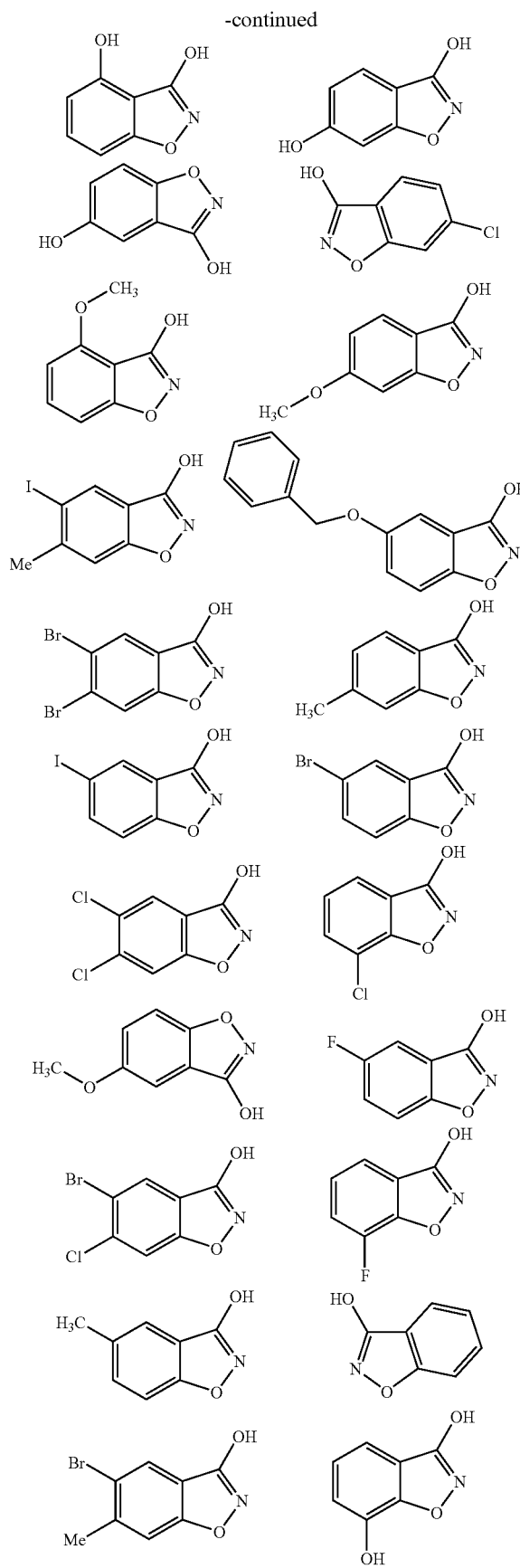
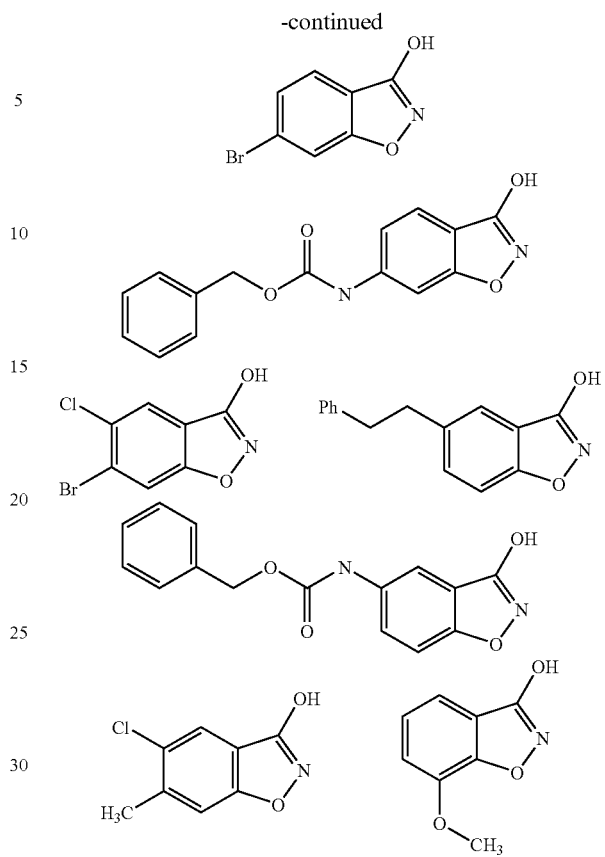

The invention includes compounds of formula I and Ia, as well as pharmaceutically acceptable salts and solvates of these compounds. The terminology "compound or a pharmaceutically acceptable salt or solvate of a compound" intends the inclusive meaning of "or", in that a material which is both a salt and a solvate is encompassed. Pharmaceutically acceptable salts include, but are not limited to, inorganic salts of aluminum, calcium, lithium, magnesium, potassium, sodium and zinc, and organic salts of lysine, N,N'-dibenzylethylene diamine, chloroprocaine, choline, diethanolamine, ethylenediamine, meglumine (N-methylglucamine), procaine and tromethamine.

Subjects for treatment according to the present invention include humans (patients) and other mammals in need of therapy for the stated condition. Patients having a need for therapy for improving or enhancing learning and memory are those exhibiting symptoms of dementia or learning and memory loss. Individuals with an amnesic disorder are impaired in their ability to learn new information or are unable to recall previously learned information or past events. The memory deficit is most apparent on tasks to require spontaneous recall and may also be evident when the examiner provides stimuli for the person to recall at a later time. The memory disturbance must be sufficiently severe to cause marked impairment in social or occupational functioning and must represent a significant decline from a previous level of functioning. The memory deficit may be age-related or the result of disease or other cause. Dementia is characterized by multiple clinically significant deficits in cognition that represent a significant change from a previous level of functioning, including memory impairment involving inability to learn new material or forgetting of previously learned material. Memory can be formally tested by measuring the ability to register, retain, recall and recognize information. A diagnosis of dementia also requires at least one of the following cognitive disturbances: aphasia, apraxia, agnosia or a disturbance in executive functioning. These deficits in language, motor performance, object recognition and abstract thinking, respectively, must be sufficiently severe in conjunction with the memory deficit to cause impairment in occupational or social functioning and must represent a decline from a previously higher level of functioning.

Compounds of formula I and Ia may also be used in conjunction with therapy involving administration of D-serine or an analog thereof, such as a salt of D-serine, an ester of D-serine, alkylated D-serine, or a precursor of D-serine, or can be used in conjunction with therapy involving administration of antipsychotics, antidepressants, psychostimulants, and/or Alzheimer's disease therapeutics.

In animals, several established models of learning and memory are available to examine the beneficial cognitive enhancing effects and potential related side effects of treatment. Descriptions of tests that may be employed to assess changes in cognition in non-human species are given in Sarter, Martin, *Intern. J. Neuroscience,* 32:765–774 (1987). The tests include the Morris water maze (Stewart and Morris, *Behavioral Neuroscience*, R. Saghal, Ed., p. 107 (1993)), delayed non-match to sample and social discrimination models.

The Morris water maze is one of the best-validated models of learning and memory, and it is sensitive to the cognitive enhancing effects of a variety of pharmacological agents. The task performed in the maze is particularly sensitive to manipulations of the hippocampus in the brain, an area of the brain important for spatial learning in animals and memory consolidation in humans. Moreover, improvement in Morris water maze performance is predictive of clinical efficacy of a compound as a cognitive enhancer. For example, treatment with cholinesterase inhibitors or selective muscarinic cholinergic agonists reverse learning deficits in the Morris maze animal model of learning and memory, as well as in clinical populations with dementia. In addition, this animal paradigm accurately models the increasing degree of impairment with advancing age and the increased vulnerability of the memory trace to pre-test delay or interference which is characteristic of amnesiac patients. The test is a simple spatial learning task in which the animal is placed in a tank of tepid water, which is opaque due to the addition of powdered milk. The animals learn the location of a-platform relative to visual cues located within the maze and the testing room; this learning is referred to as place learning. Groups of animals receive control solution or a dosage of the therapeutic agent, at the desired time interval prior to training or after training. Control animals typically reach the platform within five to ten seconds after three days of training. The measure of the memory modulator effects of a therapeutic agent is a shift of this time period. In the-second or probe phase of the test, animals which have previously learned the position of the platform are placed in the tank from which the platform has been removed. Animals that remember the position of the platform will spend more time in the quadrant that had contained the platform and will make more crossings over the position previously occupied by the platform. Increases in memory or cognitive ability are manifested by animals spending more time in the correct quadrant or making more crossing over the position previously occupied by the platform as compared with control animals. Decreases in memory or cognitive ability are manifested by animals spending less time in the correct quadrant or making less crossings of the platform position than control animals.

In the delayed non-match to sample test an animal is presented with a stimulus (for example lever A). After a period of time the animal is presented with two choices (example lever A and lever B). Selection of the choice that does not match the original stimulus (lever B) results in a reward. Greater than chance selection of the proper choice indicates that the original stimulus was remembered. As the time between stimulus and choice response is increased, performance decreases and approaches pure chance. The number of correct choices at a given time is related to cognitive ability. Deficits in cognition or memory may be induced physically, biochemically or by the use of aged animals.

In the social interaction test a foreign animal (animal B) is introduced into the home cage of the test animal (animal A). Animal A will recognize the introduced animal as foreign and investigate it. If animal B is removed and reintroduced at a later time, the test animal (animal A) will spend less time investigating the new cage mate as it remembers it from the previous introduction. As time between introductions increases, more time is spent investigating the new animal the second time as it is less well remembered. The time spent investigating the new cage mate during the second introduction is inversely related to cognitive ability. Deficits in cognition or memory may be introduced physically, biochemically or by the use of aged animals.

In humans, methods for improving learning and memory may be measured by such tests as the Wechsler Memory Scale and the Minimental test. A standard clinical test for determining if a patient has impaired learning and memory is the Minimental Test for Learning and Memory (Folstein et al., J. Psychiatric Res. 12:185, 1975), especially for those suffering from head trauma, Korsakoff's disease or stroke. The test result serves as an index of short-term, working memory of the kind that deteriorates rapidly in the early stages of dementing or amnesiac disorders. Ten pairs of unrelated words (e.g., army-table) are read to the subject. Subjects are then asked to recall the second word when given the first word of each pair. The measure of memory impairment is a reduced number of paired-associate words recalled relative to a matched control group. Improvement in learning and memory constitutes either (a) a statistically significant difference between the performance of treated patients as compared to members of a placebo group; or (b) a statistically significant change in performance in the direction of normality on measures pertinent to the disease model. Animal models or clinical instances of disease exhibit symptoms which are by definition distinguishable from normal controls. Thus, the measure of effective pharmacotherapy will be a significant, but not necessarily complete, reversal of symptoms. Improvement can be facilitated in both animal and human models of memory pathology by clinically effective "cognitive enhancing" drugs which serve to improve performance of a memory task. For example, cognitive enhancers which function as cholinomimetic replacement therapies in patients suffering from dementia and memory loss of the Alzheimer's type significantly improve short-term working memory in such paradigms as the paired-associate task. Another potential application for therapeutic interventions against memory impairment is suggested by age-related deficits in performance which are effectively modeled by the longitudinal study of recent memory in aging mice.

The Wechsler Memory Scale is a widely-used pencil-and-paper test of cognitive function and memory capacity. In the normal population, the standardized test yields a mean of 100 and a standard deviation of 15, so that a mild amnesia can be detected with a 10–15 point reduction in the score, a more severe amnesia with a 20–30 point reduction, and so forth. During the clinical interview, a battery of tests, including, but not limited to, the Minimental test, the Wechsler memory scale, or paired-associate learning are applied to diagnose symptomatic memory loss. These tests provide general sensitivity to both general cognitive impairment and specific loss of learning/memory capacity (Squire, 1987). Apart from the specific diagnosis of dementia or amnestic disorders, these clinical instruments also identify age-related cognitive decline which reflects an objective diminution in mental function consequent to the aging process that is within normal limits given the person's age (DSM IV, 1994). As noted above, "improvement" in learning and memory within the context of the present invention occurs when there is a statistically significant difference in the direction of normality in the paired-associate test, for example, between the performance of therapeutic agent treated patients as compared to members of the placebo group or between subsequent tests given to the same patient.

The prepulse inhibition test may be used to identify compounds that are effective in treating schizophrenia. The test is based upon the observations that animals or humans that are exposed to a loud sound will display a startle reflex and that animals or humans exposed to a series of lower intensity sounds prior to the higher intensity test sound will no longer display as intense of a startle reflex. This is termed prepulse inhibition. Patients diagnosed with schizophrenia display defects in prepulse inhibition, that is, the lower intensity prepulses no longer inhibit the startle reflex to the intense test sound. Similar defects in prepulse inhibition can be induced in animals via drug treatments (scopolamine, ketamine, PCP or MK801) or by rearing offspring in isolation. These defects in prepulse inhibition in animals can be partially reversed by drugs known to be efficacious in schizophrenia patients. It is felt that animal prepulse inhibition models have face value for predicting efficacy of compounds in treating schizophrenia patients.

The Spinal Nerve Ligation (SNL) model (Kim S H and Chung J M (1992) An experimental model for peripheral neuropathy produced by segmental spinal nerve ligation in the rat. *Pain* 50:355–63.) may be used to determine the effect of therapeutic agents on chronic neuropathic pain. The animals are anesthetized with isoflurane, the left L5 transverse process is removed, and the L5 and L6 spinal nerves are tightly ligated with 6-0 silk suture. The wound is then closed with internal sutures and external staples. Wound clips are removed 10–11 days following surgery. Baseline, post-injury and post-treatment values for non-noxious mechanical sensitivity are evaluated using 8 Semmes-Weinstein filaments (Stoelting, Wood Dale, Ill., USA) with varying stiffness (0.4, 0.7, 1.2, 2.0, 3.6, 5.5, 8.5, and 15 g) according to the up-down method (Chaplan S R, Bach F W, Pogrel J W, Chung J M and Yaksh T L (1994) Quantitative assessment of tactile allodynia in the rat paw. J Neurosci Methods 53:55–63.). Animals are placed on a perforated metallic platform and allowed to acclimate to their surroundings for a minimum of 30 minutes before testing. The mean and standard error of the mean (SEM) are determined for each animal in each treatment group. Since this stimulus is normally not considered painful, significant injury-induced increases in responsiveness in this test are interpreted as a measure of mechanical allodynia. Mechanical hypersensitivity of the injured paw is determined by comparing contralateral to ipsilateral paw values within the vehicle group. Data are analyzed using the Mann-Whitney test. Stability of vehicle group injured paw values over time is tested using the Friedman two-way analysis of variance by rank. Drug effect is analyzed at each time point by carrying out a Kruskal-Wallis one-way analysis of variance by rank followed by a Dunn's post hoc test or Mann-Whitney signed rank test.

If desired, compounds of formula I and Ia may also be used in conjunction with therapy involving administration of D-serine or an analog thereof, such as a salt of D-serine, an ester of D-serine, alkylated D-serine, or a precursor of D-serine. The compounds may also be used in conjunction with therapy involving administration of antipsychotics (for treating schizophrenia and other psychotic conditions), psychostimulants (for treating attention deficit disorder, depression, or learning disorders), antidepressants, nootropics (for example, piracetam, oxiracetam or aniracetam), acetylcholinesterase inhibitors (for example, the physostigmine related compounds, tacrine or donepezil) and/or Alzheimer's disease therapeutics (for treating Alzheimer's disease). Such methods for conjoint therapies are included within the invention.

The phrase "therapeutically effective amount" as used herein means that amount of a compound, material, or composition comprising a compound of the present invention which is effective for producing some desired therapeutic effect by inhibition of DAAO in at least a subpopulation of cells in an animal and thereby blocking the biological consequences of that pathway in the treated cells, at a reasonable benefit/risk ratio applicable to any medical treatment.

The term "pharmaceutically acceptable salt" refers to salts prepared from pharmaceutically acceptable non-toxic bases including inorganic bases and organic bases. Suitable pharmaceutically acceptable base addition salts for the compounds of the present invention include metallic salts made from aluminum, calcium, lithium, magnesium, potassium, sodium and zinc or organic salts made from lysine, N,N'-dibenzylethylene diamine, chloroprocaine, choline, diethanolamine, ethylenediamine, meglumine (N-methylglucamine) procaine and tromethamine.

In general, the compounds of the present invention are commercially available or may be prepared by methods well known to persons of skill in the art. In addition, methods described below, or modifications thereof, using readily available starting materials, reagents and conventional synthesis procedures may be employed. In these reactions, it is also possible to make use of variants that are in themselves known, but are not mentioned here.

In the context of the present invention, alkyl is intended to include linear, branched, or cyclic hydrocarbon structures and combinations thereof, including lower alkyl and higher alkyl. Preferred alkyl groups are those of $C_{20}$ or below. Lower alkyl refers to alkyl groups of from 1 to 6 carbon atoms, preferably from 1 to 4 carbon atoms, and includes methyl, ethyl, n-propyl, isopropyl, and n-, s- and t-butyl. Higher alkyl refers to alkyl groups having seven or more carbon atoms, preferably 7–20 carbon atoms, and includes n-, s- and t-heptyl, octyl, and dodecyl. Cycloalkyl is a subset of alkyl and includes cyclic hydrocarbon groups of from 3 to 8 carbon atoms. Examples of cycloalkyl groups include cyclopropyl, cyclobutyl, cyclopentyl, and norbornyl Aryl and heteroaryl mean a 5- or 6-membered aromatic or heteroaromatic ring containing 0–3 heteroatoms selected from nitrogen, oxygen or sulfur; a bicyclic 9- or 10-membered aromatic or heteroaromatic ring system containing 0–3 heteroatoms selected from nitrogen, oxygen or sulfur; or a tricyclic 13- or 14-membered aromatic or heteroaromatic ring system containing 0–3 heteroatoms selected from nitrogen, oxygen or sulfur. The aromatic 6- to 14-membered carbocyclic rings include, for example, benzene, naphthalene, indane, tetralin, and fluorene; and the 5- to 10-membered aromatic heterocyclic rings include, e.g., imidazole, pyridine, indole, thiophene, benzopyranone, thiazole, furan, benzimidazole, quinoline, isoquinoline, quinoxaline, pyrimidine, pyrazine, tetrazole and pyrazole.

Arylalkyl means an alkyl residue attached to an aryl ring. Examples are benzyl and phenethyl. Heteroarylalkyl means an alkyl residue attached to a heteroaryl ring. Examples include pyridinylmethyl and pyrimidinylethyl. Alkylaryl means an aryl residue having one or more alkyl groups attached thereto. Examples are tolyl and mesityl.

Alkoxy or alkoxyl refers to groups of from 1 to 8 carbon atoms of a straight, branched, cyclic configuration and combinations thereof attached to the parent structure through an oxygen. Examples include methoxy, ethoxy, propoxy, isopropoxy, cyclopropyloxy, and cyclohexyloxy. Lower alkoxy refers to groups containing one to four carbons.

Acyl refers to groups of from 1 to 8 carbon atoms of a straight, branched, cyclic configuration, saturated, unsaturated and aromatic and combinations thereof, attached to the parent structure through a carbonyl functionality. One or more carbons in the acyl residue may be replaced by nitrogen, oxygen or sulfur as long as the point of attachment to the parent remains at the carbonyl. Examples include acetyl, benzoyl, propionyl, isobutyryl, t-butoxycarbonyl, and benzyloxycarbonyl. Lower-acyl refers to groups containing one to four carbons.

Heterocycle means a cycloalkyl or aryl residue in which one to two of the carbons is replaced by a heteroatom such as oxygen, nitrogen or sulfur. Examples of heterocycles that fall within the scope of the invention include pyrrolidine, pyrazole, pyrrole, indole, quinoline, isoquinoline, tetrahydroisoquinoline, benzofuran, benzodioxan, benzodioxole (commonly referred to as methylenedioxyphenyl, when occurring as a substituent), tetrazole, morpholine, thiazole, pyridine, pyridazine, pyrimidine, thiophene, furan, oxazole, oxazoline, isoxazole, dioxane, and tetrahydrofuran.

Substituted refers to residues, including, but not limited to, alkyl, alkylaryl, aryl, arylalkyl, and heteroaryl, wherein up to three H atoms of the residue are replaced with lower alkyl, substituted alkyl, substituted alkynyl, haloalkyl, alkoxy, carbonyl, carboxy, carboxalkoxy, carboxamido, acyloxy, amidino, nitro, halogen, hydroxy, $OCH(COOH)_2$, cyano, primary amino, secondary amino, acylamino, alkylthio, sulfoxide, sulfone, phenyl, benzyl, phenoxy, benzyloxy, heteroaryl, or heteroaryloxy.

Haloalkyl refers to an alkyl residue, wherein one or more H atoms are replaced by halogen atoms; the term haloalkyl includes perhaloalkyl. Examples of haloalkyl groups that fall within the scope of the invention include $CH_2F$, $CHF_2$, and $CF_3$.

In the context of the present invention, compounds that are considered to possess activity as DAAO inhibitors are those displaying 50% inhibition of the enzymatic cycle of DAAO ($IC_{50}$) a concentration of about $\leq 100$ μM, preferably, about $\leq 10$ μM and more preferably about $\leq 1$ μM.

Many of the compounds described herein may contain one or more asymmetric centers and may thus give rise to enantiomers, diastereomers, and other stereoisomeric forms that may be defined, in terms of absolute stereochemistry, as (R)— or (S)—. The present invention is meant to include all such possible isomers, as well as, their racemic and optically pure forms. Optically active (R)— and (S)— isomers may be prepared using chiral synthons or chiral reagents, or resolved using conventional techniques. When the compounds described herein contain olefinic double bonds or other centers of geometric asymmetry, and unless specified otherwise, it is intended that the compounds include both E and Z geometric isomers. Likewise, all tautomeric forms are also intended to be included.

While it may be possible for compounds of formula I and Ia to be administered as the raw chemical, it is preferable to present them as a pharmaceutical composition. According to a further aspect, the present invention provides a pharmaceutical composition comprising a compound of formula I and Ia or a pharmaceutically acceptable salt or solvate thereof, together with one or more pharmaceutically carriers thereof and optionally one or more other therapeutic ingredients. The carrier(s) must be "acceptable" in the sense of being compatible with the other ingredients of the formulation and not deleterious to the recipient thereof.

The formulations include those suitable for oral, parenteral (including subcutaneous, intradermal, intramuscular, intravenous and intraarticular), rectal and topical (including dermal, buccal, sublingual and intraocular) administration. The most suitable route may depend upon the condition and disorder of the recipient. The formulations may conveniently be presented in unit dosage form and may be prepared by any of the methods well known in the art of pharmacy. All methods include the step of bringing into association a compound or a pharmaceutically acceptable salt or solvate thereof ("active ingredient") with the carrier which constitutes one or more accessory ingredients. In general, the formulations are prepared by uniformly and intimately bringing into association the active ingredient with liquid carriers or finely divided solid carriers or both and then, if necessary, shaping the product into the desired formulation. Oral formulations, are well known to those skilled in the art, and general methods for preparing them are found in any standard pharmacy school textbook, for example, *Remington: The Science and Practice of Pharmacy*, A. R. Gennaro, ed. (1995), the entire disclosure of which is incorporated herein by reference.

Formulations of the present invention suitable for oral administration may be presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion. The active ingredient may also be presented as a bolus, electuary or paste.

A tablet may be made by compression or molding, optionally with one or more accessory ingredients. Compressed tablets may be prepared by compressing in a suitable machine the active ingredient in a free-flowing form such as a powder or granules, optionally mixed with a binder, lubricant, inert diluent, lubricating, surface active or dispersing agent. Molded tablets may be made by molding in a suitable machine a mixture of the powdered compound moistened with an inert liquid diluent. The tablets may optionally be coated or scored and may be formulated so as to provide sustained, delayed or controlled release of the active ingredient therein. Oral and parenteral sustained release drug delivery systems are well known to those skilled in the art, and general methods of achieving sustained release of orally or parenterally administered drugs are found, for example, in *Remington: The Science and Practice of Pharmacy*, pages 1660–1675 (1995).

Formulations for parenteral administration include aqueous and non-aqueous sterile injection solutions which may contain anti-oxidants, buffers, bacteriostats and solutes which render the formulation isotonic with the blood of the intended recipient. Formulations for parenteral administration also include aqueous and non-aqueous sterile suspensions, which may include suspending agents and thickening agents. The formulations may be presented in unit-dose of multi-dose containers, for example sealed ampoules and vials, and may be stored in a freeze-dried (lyophilized) condition requiring only the addition of a sterile liquid carrier, for example saline, phosphate-buffered saline (PBS) or the like, immediately prior to use. Extemporaneous injection solutions and suspensions may be prepared from sterile powders, granules and tablets of the kind previously described. Formulations for rectal administration may be presented as a suppository with the usual carriers such as cocoa butter or polyethylene glycol. Formulations for topical administration in the mouth, for example, buccally or sublingually, include lozenges comprising the active ingredient in a flavored basis such as sucrose and acacia or tragacanth, and pastilles comprising the active ingredient in a basis such as gelatin and glycerin or sucrose and acacia.

Pharmaceutical compositions containing compounds of formula I and Ia may be conveniently presented in unit dosage form and prepared by any of the methods well known in the art of pharmacy. Preferred unit dosage formulations are those containing an effective dose, or an appropriate fraction thereof, of the active ingredient, or a pharmaceutically acceptable salt thereof. The magnitude of a prophylactic or therapeutic dose typically varies with the nature and severity of the condition to be treated and the route of administration. The dose, and perhaps the dose frequency, will also vary according to the age, body weight and response of the individual patient. In general, the total daily dose ranges from about 1 mg per day to about 7000 mg per day, preferably about 1 mg per day to about 100 mg per day, and more preferably, about 25 mg per day to about 50 mg per day, in single or divided doses. In some embodiments, the total daily dose may range from about 50 mg to about 500 mg per day, and preferably, about 100 mg to about 500 mg per day. It is further recommended that children, patients over 65 years old, and those with impaired renal or hepatic function, initially receive low doses and that the dosage be titrated based on individual responses and blood levels. It may be necessary to use dosages outside these ranges in some cases, as will be apparent to those in the art. Further, it is noted that the clinician or treating physician knows how and when to interrupt, adjust or terminate therapy in conjunction with individual patient's response.

It should be understood that in addition to the ingredients particularly mentioned above, the formulations of this invention may include other agents conventional in the art having regard to the type of formulation in question, for example those suitable for oral administration may include flavoring agents.

EXAMPLES

Example 1

General Procedure for Preparation of Benzo[d]isoxazol-3-ols

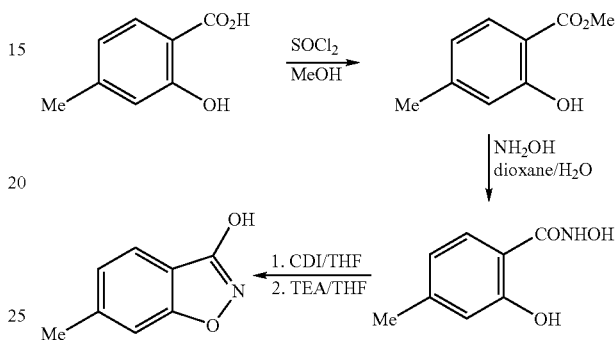

2-Hydroxy-4-methyl-benzoic acid methyl ester: A 50 ml round-bottom flask equipped with a stir bar under a dry nitrogen atmosphere was charged with 4-methylsalicylic acid (1.5 g, 10.0 mmoles, 1.0 eq) followed by dry MeOH (15 ml). The reaction mixture was cooled to 0° C. on an ice bath and neat $SOCl_2$ (1.1 ml, 15.0 mmoles, 1.5 eq) was added dropwise. The reaction was allowed to warm to room temperature and then stirred at reflux for 5 hrs. After that time, excess MeOH was removed in vacuo, the residue dissolved in EtOAc and extracted with saturated $NaHCO_3$, the organic layer was dried with $MgSO_4$ and filtered. Removal of excess solvent from the filtrate in vacuo provided 1.20 g (72%) of the title compound as a clear oil. ($^1$H $CDCl_3$, 400 MHz): δ 10.71 (s, 1H), 7.70 (d, J=8.1 Hz, 1H), 6.75 (s, 1H), 6.69 (d, J=8.1 Hz, 1H), 3.93 (s, 3H), 2.34 (s, 3H).

2-N-Dihydroxy-4-methyl-benzamide: A 250 ml round-bottom flask equipped with a stir bar was charged with hydroxylamine hydrochloride (3.5 g, 50.0 mmoles, 25.0 eq) followed by $H_2O$ (35 ml) and by an aqueous solution of NaOH (3.0M/$H_2O$, 38 ml, 114 mmoles, 57.0 eq). In a separate flask, the crude 2-Hydroxy-4-methyl-benzoic acid methyl ester (332 mg, 2.0 mmoles, 1.0 eq) was dissolved in dioxane and added dropwise to the above solution. The reaction mixture was stirred at room temperature for 20 hrs, cooled to 0° C. on an ice bath and neutralized to pH=5 (pH paper strips) with conc. aqueous HCl (10.0M/$H_2O$). The reaction was allowed to warm to room temperature, EtOAc was added, the crude product was partitioned in a separatory funnel (3×EtOAc), the organic layer was dried with $MgSO_4$ and filtered. Removal of excess solvent from the filtrate in vacuo provided 331 mg (99%) of the title compound as an off-white solid. ($^1$H DMSO-$d_6$, 400 MHz) δ 12.29 (s, 1H), 11.37 (s, 1H), 9.26 (s, 1H), 7.54 (d, J=8.0 Hz, 1H) 6.70 (s, 1H), 6.648 (d, J=8.1 Hz, 1H), 2.24 (s, 3H).

6-Methyl-benzo[d]isoxazol-3-ol: A 50 ml round-bottom flask equipped with a stir bar under a dry nitrogen atmosphere was charged with 2-N-Dihydroxy-4-methyl-benzamide (331 mg, 2.0 mmole, 1.0 eq) and carbonyldiimidazole (1.0 g, 6.0 mmoles, 3.0 eq) followed by dry THF (20 ml).

The reaction mixture was stirred at reflux for 30 minutes and then neat TEA (415 μL, 3.0 mmoles, 1.5 eq) was added. The reaction mixture was refluxed for additional 20 hrs, cooled to room temperature and excess THF was removed in vacuo. The residue was dissolved in EtOAc, extracted with aqueous HCl (1.0M/H$_2$O), the organic layer was dried with MgSO$_4$, filtered and excess solvent from the filtrate was removed in vacuo. Purification of the crude product by flash chromatography (silica gel, 0%→40% gradient of 2% AcOH/EtOAc in hexanes) provided 167 mg (56%) as a white solid. ($^1$H DMSO-d$_6$, 400 MHz) δ 12.19 (s, 1H), 7.59 (d, J=8.0 Hz, 1H), 7.34 (s, 1H), 7.12 (d, J=8.0 Hz, 1H), 2.07 (s, 3H); ($^{13}$C DMSO-d$_6$, 100 MHz) δ 165.09, 163.59, 141.18, 124.588, 120.76, 112.08, 109.80, 21.33.

5-Methyl-benzo[d]isoxazol-3-ol: The title compound was prepared from commercially available 2-N-Dihydroxy-5-methyl-benzamide as described above. ($^1$H DMSO-d$_6$, 400 MHz) δ 12.19 (s, 1H), 7.48 (s, 1H), 7.42–7.40 (m, 2H), 2.38 (s, 3H); ($^{13}$C DMSO-d$_6$, 100 MHz) δ 165.01, 161.61, 132.22, 131.92, 120.38, 114.47, 109.64, 20.45.

5-Chloro-benzo[d]isoxazol-3-ol: The title compound was prepared from commercially available 2-N-Dihydroxy-5-chloro-benzamide as described above. ($^1$H DMSO-d$_6$, 400 MHz) δ 12.55 (s, 1H), 7.78, (s, 1H), 7.60 (m, 2H); ($^{13}$C DMSO-d$_6$, 100 MHz) δ 164.67, 161.65, 130.66, 127.17, 120.63, 115.90, 111.88.

5-Methoxy-benzo[d]isoxazol-3-ol: The title compound was prepared from commercially available 2-Hydroxy-5-methoxy-benzoic acid methyl ester as described above. ($^1$H DMSO-d$_6$, 400 MHz) δ 12.21 (s, 1H), 7.45 (d, J=9.0 Hz, 1H), 7.18 (dd, J=9.5 Hz, J'=11.5 Hz, 1H), 7.14 (d, J'=11.5 Hz), 3.80 (d, J'=11.5 Hz, 3H); ($^{13}$C DMSO-d$_6$, 100 MHz) δ 165.23, 158.26, 155.44, 120.50, 114.51, 110.90, 101.60, 55.67.

5-Hydroxy-benzo[d]isoxazol-3-ol: The title compound was prepared from commercially available 2,5-Dihydroxy-benzoic acid methyl ester as described above. ($^1$H DMSO-d$_6$, 400 MHz) δ 12.03 (s, 1H), 9.55 (s, 1H), 7.34 (d, J=9.0 Hz, 1H) 7.02 (dd, J=9.4 Hz, J'=2.4 Hz, 1H), 6.94 (d, J=2.4 Hz, 1H); ($^{13}$C DMSO-d$_6$, 100 MHz) δ 164.97, 157.41, 153.22, 120.14, 114.74, 110.52, 103.89.

6-Hydroxy-benzo[d]isoxazol-3-ol: The title compound was prepared from commercially available 2,4-Dihydroxy-benzoic acid methyl ester as described above. ($^1$H DMSO-d$_6$, 400 MHz) δ 12.00 (s, 1H), 10.29 (s, 1H), 7.49 (d, J=9.1 Hz, 1H), 6.75–6.73 (m, 2H); ($^{13}$C DMSO-d$_6$, 100 MHz) δ 165.17, 164.91, 160.57, 121.90, 113.13, 106.52, 95.10.

5-Bromo-benzo[d]isoxazol-3-ol: The title compound was prepared from commercially available 5-bromo-2-hydroxy-benzoic acid as described above. ($^1$H DMSO-d$_6$, 400 MHz) δ 12.55 (s, 1H), 7.93 (d, J=1.8 Hz, 1H), 7.73 (dd, J=1.8 Hz, J'=8.9 Hz), 7.56 (d, J'=8.8 Hz); ($^{13}$C DMSO-d$_6$, 100 MHz) δ 164.48, 161.98, 133.26, 123.70, 116.52, 114.76, 112.29.

7-Methoxy-benzo[d]isoxazol-3-ol: The title compound was prepared from commercially available 2-Hydroxy-3-methoxy-benzoic acid methyl ester as described above. ($^1$H DMSO-d$_6$, 400 MHz) δ 12.29 (s, 1H), 7.26–7.13 (m, 3H), 3.92 (s, 3H); ($^{13}$C DMSO-d$_6$, 100 MHz) δ 165.48, 153.07, 143.98, 124.17, 115.95, 112.41, 111.57, 55.97.

4-Hydroxy-benzo[d]isoxazol-3-ol: The title compound was prepared from commercially available 2,6-Dihydroxy-benzoic acid methyl ester as described above. ($^1$H DMSO-d$_6$, 400 MHz) δ 11.90 (s, 1H), 10.49 (s, 1H), 7.30 (t, J=8.0 Hz, J'=8.2 Hz, 1H), 6.85 (d, J=8.3 Hz, 1H), 6.55 (d, J=7.9 Hz, 1H); ($^{13}$C DMSO-d$_6$, 100 MHz) δ 165.24, 164.89, 153.41, 132.00, 107.55, 103.44, 100.24.

6-Fluoro-benzo[d]isoxazol-3-ol: The title compound was prepared from commercially available 4-fluoro-2-hydroxy-benzoic acid methyl ester as described above. ($^1$H DMSO-d$_6$, 400 MHz) δ 12.47 (s, 1H), 7.77 (dd, $^4$J(H,F)=5.4 Hz, J=8.7 Hz, 1H), 7.53 (dd, J'=1.7 Hz, $^3$J(H,F)=10.0 Hz, 1H), 7.19 (dt J'=1.4 Hz, $^3$J(H,F)=9.5 Hz, J=9.0 Hz, 1H); ($^{13}$C DMSO-d$_6$, 100 MHz) δ 165.02, 163.65 (d, $^3$J(C,F)=14 Hz), 163.33 (d, $^1$J(C,F)=247 Hz), 122.90 (d, $^3$J(C,F)=11 Hz), 111.97 (d, $^2$J(C,F)=26 Hz), 111.27, 97.70 (d, $^2$J(C,F)=27 Hz).

4-Fluoro-benzo[d]isoxazol-3-ol: The title compound was prepared from commercially available 6-fluoro-2-hydroxy-benzoic acid methyl ester as described above. ($^1$H DMSO-d$_6$, 400 MHz) δ 12.69 (s, 1H), 7.60 (dt, $^4$J(H,F)=5.4 Hz, J=8.2 Hz, J'=8.2 Hz, 1H), 7.40 (d, J=8.5 Hz, 1H), 7.19 (t, $^3$J(H,F)=9.7 Hz, J=8.1 Hz, 1H); ($^{13}$C DMSO-d$_6$, 100 MHz) δ 165.15, 163.45, 155.13 (d, $^1$J(C,F)=254 Hz), 132.50 (d, $^3$J(C,F)=18 Hz), 108.55 (d, $^2$J(C,F)=18 Hz), 106.74, 106.78.

6-Methoxy-benzo[d]isoxazol-3-ol: The title compound was prepared from commercially available 2-Hydroxy-4-methoxy-benzoic acid methyl ester as described above. ($^1$H DMSO-d$_6$, 400 MHz) δ 12.14 (s, 1H), 7.56 (d, J=8.6 Hz, 1H), 7.09 (d, J'=1.9 Hz, 1H), 6.87 (dd, J=8.7 Hz, J'=1.9 Hz, 1H), 3.82 (s, 3H); ($^{13}$C DMSO-d$_6$, 100 MHz) δ 165.08, 164.99, 162.23, 121.68, 113.21, 107.43, 93.34, 55.79.

4-Methoxy-benzo[d]isoxazol-3-ol: The title compound was prepared from commercially available 2-Hydroxy-6-methoxy-benzoic acid as described above. ($^1$H CD$_3$OD, 400 MHz) δ 7.52 (t, J=J'=8.2 Hz, 1H), 7.01 (d, J=8.4 Hz, 1H), 6.74 (d, J'=8.0 Hz, 1H), 3.96 (s, 3H); ($^{13}$C CD$_3$OD, 100 MHz) δ 165.83, 165.37, 155.89, 132.83, 104.28, 103.26, 102.25, 55.12.

5-Fluoro-benzo[d]isoxazol-3-ol: The title compound was prepared from commercially available 5-fluoro-2-hydroxy-benzoic acid as described above. ($^1$H DMSO-d$_6$, 400 MHz) δ 12.48 (s, 1H), 7.61 (dd, $^4$J(H,F)=5.3 Hz, J=9.0 Hz, 1H), 7.53 (dd, J'=2.2 Hz, $^3$J(H,F)=7.7 Hz, 1H), 7.49 (dt J'=2.2 Hz, $^3$J(H,F)=9.0 Hz, J=9.0 Hz, 1H); ($^{13}$C DMSO-d$_6$, 100 MHz) δ 165.31, 159.62, 158.02 (d, $^1$J(C,F)=238 Hz), 119.00 (d, $^2$J(C,F)=27 Hz), 111.61 (d, $^3$J(C,F)=9 Hz), 106.47, 106.22.

6-Bromo-benzo[d]isoxazol-3-ol: The title compound was prepared from 6-bromo-2-hydroxy-benzoic acid (*J. Med. Chem.* (1992), 35, 739) as described above. ($^1$H CD$_3$OD, 400 MHz) δ 7.71 (s, 1H), 7.61 (d, J=8.3 Hz, 1H), 7.45 (d, J=8.3 Hz, 1H); ($^{13}$C CD$_3$OD, 100 MHz) δ 166.77, 165.43, 127.79, 126.08 123.62, 115.27, 114.56.

7-Fluoro-benzo[d]isoxazol-3-ol: The title compound was prepared from commercially available 3-fluoro-2-hydroxy-benzoic acid as described above. ($^1$H DMSO-d$_6$, 400 MHz) δ 12.73 (s, 1H), 7.57 (d, J=7.9 Hz, 1H), 7.53 (dd, $^3$J(H,F)=11.3 Hz, J=8.0 Hz, 1H) 7.31 (dt, $^4$J(H,F)=4.0 Hz, J=7.9 Hz, J'=7.9 Hz, 1H); ($^{13}$C CD$_3$OD, 100 MHz) δ 167.05 (d, $^4$J(C,F)=3 Hz), 152.49 (d, $^2$J(C,F)=14 Hz), 147.88 (d, $^1$J(C,F)=249 Hz), 125.22 (d, $^3$J(C,F)=5 Hz), 119.92 (d, $^4$J(C,F)=3 Hz), 118.13 (d, $^3$J(C,F)=5 Hz), 117.11 (d, $^2$J(C,F)=14 Hz).

7-Chloro-benzo[d]isoxazol-3-ol: The title compound was prepared from commercially available 3-chloro-2-hydroxy-benzoic acid as described above. ($^1$H DMSO-d$_6$, 400 MHz) δ 12.74 (s, 1H), 7.74, (s, 1H), 7.72 (s, 1H), 7.33 (t, J=J'=7.8 Hz, 1H); ($^{13}$C CD$_3$OD, 100 MHz) δ 167.18, 160.58, 131.51, 125.37, 121.18, 117.87, 116.71.

7-Hydroxy-benzo[d]isoxazol-3-ol: The title compound was prepared from commercially available 2,3-Dihydroxy-benzoic acid as described above. ($^1$H DMSO-d$_6$, 400 MHz) δ 12.17 (s, 1H), 10.37 (s, 1H), 7.11 (dd, J=8.0 Hz, J'=1.7 Hz, 1H), 7.07 (t, J=J'=7.7 Hz, 1H), 6.93 (dd, J=8.0 Hz, J'=1.7 Hz, 1H); ($^{13}$C CD$_3$OD, 100 MHz) δ 167.29, 154.69, 143.12, 125.26, 117.58, 116.69, 112.51.

5-Iodo-benzo[d]isoxazol-3-ol: The title compound was prepared from commercially available 5-iodo-2-hydroxybenzoic acid as described above. ($^1$H DMSO-d$_6$, 400 MHz) δ 12.48 (s, 1H), 8.08 (s, 1H), 7.85 (d, J=8.8 Hz, 1H), 7.42 (d, J=8.7 Hz, 1H); ($^{13}$C DMSO-d$_6$, 100 MHz) δ 164.11, 162.43, 138.62, 129.68, 117.15, 112.49, 86.28.

Example 2

General Procedure for Bromination of Benzo[d]isoxazol-3-ols

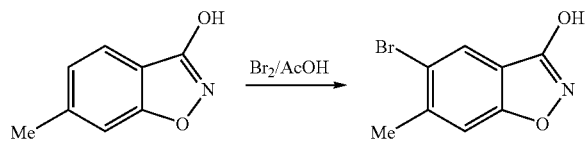

5-Bromo-6-methyl-benzo[d]isoxazol-3-ol: A 25 ml high-pressure tube equipped with a stir bar and a screw-on Teflon cap was charged with 6-methyl-benzo[d]isoxazol-3-ol (745 mg, 5.0 mmole, 1.0 eq) and glacial acetic acid (5.0 ml). Neat Br$_2$ (774 μL, 15.0 mmoles, 3.0 eq) was added dropwise. After stirring at 80° C. for 20 hours, the reaction was allowed to cool slowly to room temperature. The resulting precipitate was collected by filtration and washed quickly with 3×1.0 ml of glacial acetic acid. Crystallization of this crude product (624 mg) from 50 ml of MeCN yielded 567 mg of the title compound (96% purity determined RP-HPLC). Additional crystallization from 70 ml of toluene provided 519 mg (46%) as a white solid (98.1% purity determined by HPLC). ($^1$H DMSO-d$_6$, 400 MHz) δ 12.45 (s, 1H), 7.94 (s, 1H), 7.61 (s, 1H), 2.45 (s, 3H); ($^{13}$C CD$_3$OD, 100 MHz) δ 165.96, 164.50, 142.34, 125.39, 119.73, 115.78, 112.67, 24.10.

5,6-dibromo-benzo[d]isoxazol-3-ol: The title compound was prepared by bromination as described above. ($^1$H DMSO-d$_6$, 400 MHz) δ 12.72 (s, 1H), 8.15 (s, 1H), 8.12 (s, 1H); ($^{13}$C CD$_3$OD, 100 MHz) δ 165.90, 164.04, 117.33, 116.46, 128.08, 126.48, 119.30.

5-bromo-6-chloro-benzo[d]isoxazol-3-ol: The title compound was prepared by bromination as described above. ($^1$H DMSO-d$_6$, 400 MHz) δ 12.71 (s, 1H), 8.13 (s, 1H), 8.03 (s, 1H);($^{13}$C CD$_3$OD, 100 MHz)δ 165.83, 164.03, 137.92, 126.71, 117.19, 116.71, 113.14.

Example 3

General Procedure for Chlorination of Benzo[d]isoxazol-3-oles

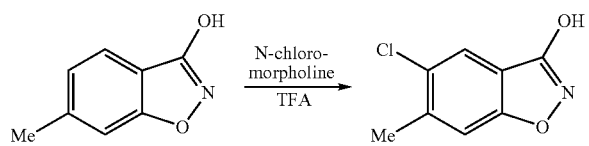

5-Chloro-6-methyl-benzo[d]isoxazol-3-ol: A 25 ml round-bottom flask equipped with a stir bar was charged with 6-methyl-benzo[d]isoxazol-3-ol (298 mg, 2.0 mmole, 1.0 eq) and TFA (2.0 ml) and cooled to 0° C. in an ice bath. Neat N-chloromorpholine (242 μL, 2.0 mmoles, 1.0 eq, *Organic Syntheses*, CV 8, 167) was added dropwise and the reaction mixture was allowed to warm to room temperature over the period of 30 minutes. EtOAc was added, the crude product was partitioned in a separatory funnel (EtOAc/1.0M aqueous HCl), the organic layer was dried with MgSO$_4$ and excess solvent was removed from the filtrate in vacuo. Crystallization of the crude product (383 mg) from a mixture of 20 ml of toluene and 6 ml of EtOAc provided 206 mg (94% purity determined by HPLC) as a white solid. ($^1$H DMSO-d$_6$, 400 MHz) δ 12.41 (s, 1H), 7.77 (s, 1H), 7.59 (s, 1H), 2.43 (s, 3H); ($^{13}$C DMSO-d$_6$, 100 MHz) δ 164.46, 161.87, 138.53, 128.08, 120.59, 113.78, 111.83, 20.49.

5,6-dichloro-benzo[d]isoxazol-3-ol: The title compound was prepared by chlorination as described above. ($^1$H DMSO-d$_6$, 400 MHz) δ 12.73 (s, 1H), 8.03 (s, 1H), 8.01 (s, 1H); ($^{13}$C DMSO-d$_6$, 100 MHz) δ 164.46, 161.39, 133.60, 125.82, 122.27, 114.85, 112.40.

5-chloro-6-bromo-benzo[d]isoxazol-3-ol: The title compound was prepared by chlorination as described above. ($^1$H DMSO-d$_6$, 400 MHz) δ 12.74 (s, 1H), 8.16 (s, 1H), 7.99 (s, 1H);($^{13}$CCD$_3$OD 100 MHz) δ 166.11, 163.47, 130.04, 126.00, 122.95, 116.87, 116.53.

Example 4

General Procedure for Iodination of Benzo[d]isoxazol-3-oles

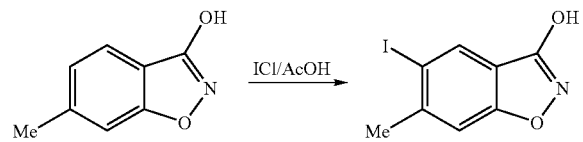

5-Iodo-6-methyl-benzo[d]isoxazol-3-ol: A 25 ml high-pressure tube equipped with a stir bar and a screw-on Teflon cap was charged with solid ICl (648 mg, 4.0 mmoles, 2.0 eq) and AcOH (6.0 ml). Solid 6-methyl-benzo[d]isoxazol-3-ol (298 mg, 2.0 mmole, 1.0 eq) was added in one portion followed by water (15 ml). The heterogeneous reaction mixture was stirred at 80° C. for 64 hours. Solid precipitate was removed by filtration, EtOAc was added to the filtrate, the crude product was partitioned in a separatory funnel (EtOAc/1.0M aqueous HCl), the organic layer was dried with MgSO$_4$ and excess solvent was removed from the filtrate in vacuo. Double recrystallization of the combined precipitate and crude product after aqueous workup (471 mg) from 15 ml and 10 ml of toluene, respectively, provided 106 mg (19%) (92% purity determined by HPLC) as a white solid. ($^1$H DMSO-d$_6$, 400 MHz) δ 12.35 (s, 1H), 8.16 (s, 1H), 7.60 (s, 1H), 2.48 (s, overlapping with DMSO-d$_6$); ($^{13}$C DMSO-d$_6$, 100 MHz) δ 163.76, 163.37, 142.88, 130.47, 114.87, 110.72, 93.42, 28.204.

Example 4

In Vitro Measurements of DAAO Activity

Purified pig DAAO, added to a buffered mixture of 50 mM D-Serine produces H$_2$O$_2$ in stoichiometric amounts for each D-Serine molecule oxidized. H$_2$O$_2$ production can be monitored with a commercially available dye Amplex Red, which in the presence of $H_2O_2$, is converted to the fluorescent product resorufin. For each described inhibitor, the fluorescence was also measured during additions of 80 μM $H_2O_2$ in the absence of DAAO, to control for artifactual inhibition of the dye conversion, and to quantify the amount of $H_2O_2$ produced. In an alternative assay of DAAO activity, the purified pig DAAO is added to buffered mixture of 1 mM phenylglycine in the presence of compounds. The activity of DAAO is monitored spectrophotometrically by its enzymatic conversion of phenylglycine to benzoylformic acid with optical absorption at 252 nm.

Inhibitors of DAAO's enzymatic cycle were serially diluted to reduce the level of inhibition. The parameters of a non-linear equation were adjusted to fit the resulting series of inhibition levels to extrapolate the concentration of compound where 50% inhibition is achieved ($IC_{50}$). These numbers are averaged for the number (n) of independent measurements (on separate days) of the inhibition.

TABLE 1

| COMPOUND | Inhibition of DAAO, $IC_{50}$ |
|---|---|
| 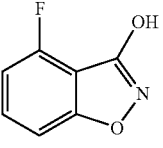 | <10 μM |
| 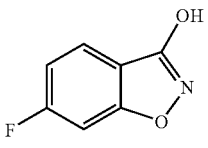 | >100 μM |
| 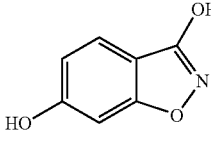 | <100 μM |
| 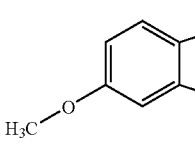 | <100 nM |
| 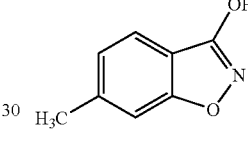 | <100 nM |
| 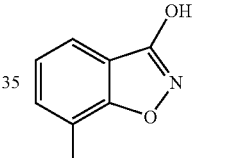 | <100 nM |
| 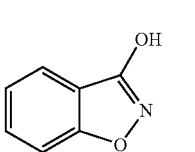 | <100 nM |

TABLE 1-continued

| COMPOUND | Inhibition of DAAO, $IC_{50}$ |
|---|---|
| 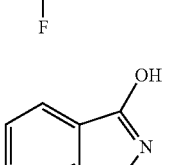 | <1 μM |
| 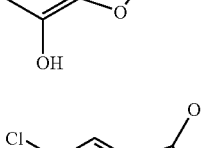 | <10 μM |
| 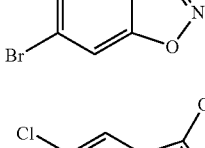 | <10 μM |
| 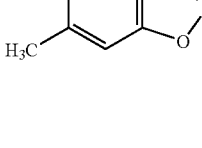 | <1 μM |
|  | >100 μM |
| 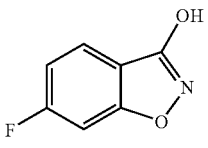 | <100 μM |
| 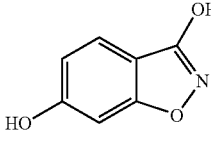 | <100 μM |
| 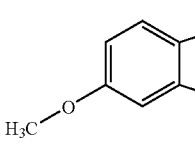 | <100 nM |
| 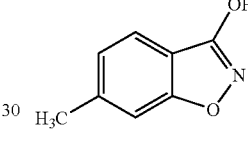 | <100 nM |

TABLE 1-continued
| COMPOUND | Inhibition of DAAO, IC$_{50}$ |
|---|---|
| 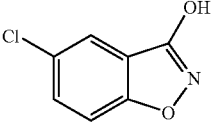 | <1 μM |
| 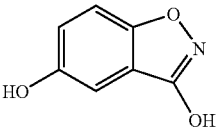 | >100 μM |
| 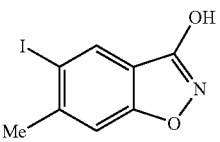 | <100 nM |
| 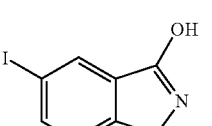 | <10 μM |
| 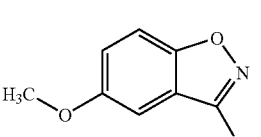 | <10 μM |
| 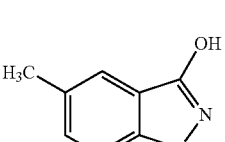 | <10 μM |
| 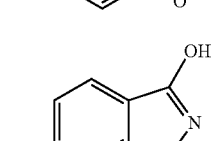 | <1 μM |
| 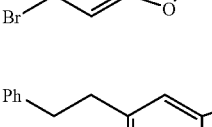 | <100 μM |
| 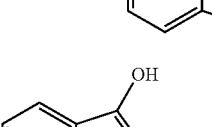 | <100 μM |
| 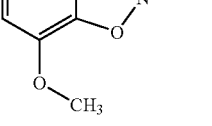 | <100 μM |
| 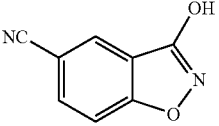 | <100 nM |
| 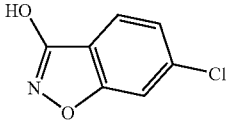 | <10 μM |
| 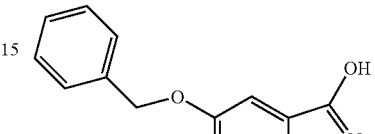 | <1 μM |
| 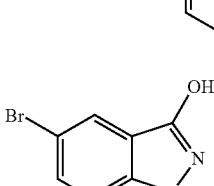 | <1 μM |
| 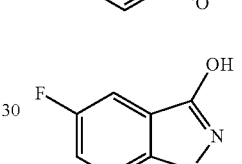 | <1 μM |
| 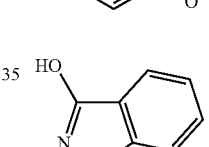 | >100 μM |
| PYRROLE-2-CARBOXYLIC ACID | <10 μM |
| INDOLE-2-CARBOXYLIC ACID | <10 μM |
| 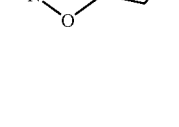 | >100 μM |
| 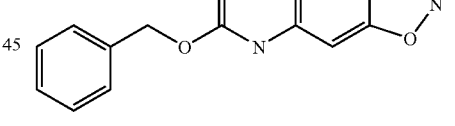 | >100 μM |

TABLE 1-continued

| COMPOUND | Inhibition of DAAO, IC$_{50}$ |
|---|---|
| (structure: 6-benzyloxy-benzo[d]isoxazol-3-ol) | >100 μM |

It can be seen from Table 1 that the IC$_{50}$ values of previously reported DAAO inhibitors are all greater than 1 μM compound for greater than 50% inhibition of DAAO activity. The benzisoxazole derivatives of the present invention display at least this much inhibitory activity, and several individual examples are 5-fold or greater more active, requiring less than 200 nM of the compounds to inhibit 50% of DAAO activity.

Example 5

Measurements of NMDA Receptor Affinity

To measure the affinity of the compounds reported herein for D-Serine's binding site on the NMDA receptor (also known as the "Glycine site" or the "strychnine-insensitive glycine site"), a radioligand-binding assay was performed with membranes prepared from rat cerebral cortex. The radioactive ligand was [3H]MDL105,519. The amount of radioactivity displaced by the compounds was assessed by scintillation counting. Non-specific binding is accounted for in the presence of 1 mM Glycine. Affinities are calculated from the values of % inhibition of specific [3H]MDL105,519 binding by the test compounds.

Indole-2-carboxylic acid inhibited 77% of specific binding of the radiolabeled compound when tested at 100 μM, while the following compound, exemplary of substituted benzo[d]isoxazol-3-ol, demonstrated no affinity (less than 10% inhibition of [3H]MDL-509,519 specific binding when tested at 100 μM) for the D-Serine binding site of the NMDA receptor:

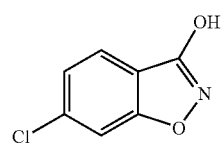

Example 6

Measurements of Rat Brain Uptake

Experiments that evaluate the rat brain penetration of test compounds use a perfusion system where the left carotid artery is cannulated and the branch arteries are tied off. The test compound plus internal controls are perfused for 30 seconds into the left hemisphere in phosphate buffered saline at pH 7.4. The internal controls are atenolol (with low brain uptake) and antipyrine (with high brain uptake). After a 30 second washout with perfusate, the brain is removed surgically. The left hemisphere is homogenized; test compounds (plus internal controls) are extracted from brain homogenate, and analyzed using LC/MS/MS to determine the concentration of test compound and internal controls in the brain. Brain uptake rates for selected compounds, expressed as pmol/g brain/sec±SD for N of 4 rats, are shown in Table 2.

TABLE 2

| Compound | Rat Brain Uptake Rate, pmol/g brain/sec |
|---|---|
| (6-methyl-benzo[d]isoxazol-3-ol) | 199 |
| (6-chloro-benzo[d]isoxazol-3-ol) | 162 |

Example 7

Measurements of Brain D-Serine Levels

Measurements of d-serine in the brains of mammals indicate that the level of endogenous production is balanced by degradation of d-serine. D-serine is produced from l-serine by the action of serine racemase, while d-serine is metabolized by the action of DAAO. Exogenously administered d-serine produces short lasting increases in brain d-serine due to the action of DAAO. Likewise, inhibitors of DAAO are shown in this invention to increase several-fold brain levels of d-serine. The clinical utility of exogenously-administered d-serine has been demonstrated in schizophrenics; see Coyle, Joseph J., *Ann. N.Y. Acad. Sci.,* 1003: 318–327 (2003) and U.S. Pat. Nos. 6,227,875; 6,420,351; and 6,667,297. Therefore, measurements of brain d-serine levels in rats are useful for assessing the potential therapeutic action of DAAO inhibitors on increases in d-serine for the treatment of schizophrenia.

In vivo increase in brain D-Serine Compounds were suspended in phosphate buffered saline (pH 7.4 with 2% Tween80) and were administered intraperitoneally into adult male Sprague Daly rats (40–60 days old, Charles River Laboratories, Inc.) weighing 185–225 g at the time of the experiment. After several hours, the rats were killed by decapitation and the cerebellum was rapidly removed and frozen to −80 C for further analysis. The remainder of the brain was likewise removed and frozen. On the day of the analysis, the brain tissue was homogenized in 5 times its volume in ice-cold 5% trichloroacetic acid. The homogenate was centrifuged at 18,000 times gravity for 30 minutes. Pellets were discarded. The supernatant was washed 3 times with water-saturated diethyl ether, discarding the organic layer. After filtration of the aqueous layer through a 0.45 μm pore size filter membrane, the samples were ready for derivatization with o-phthaldialdehyde (OPA) and BOC L-Cys-OH according to the methods of Hashimoto and colleagues (Hashimoto A, et al., J Chromatogr., 582(1–2): 41–8 (1992)). Briefly, 50 mg o each derivatization reagent were dissolved in 5 ml of methanol. A 200 µl aliquot of this was added to 100 µl of sample dissolved in 700 µl of borate buffer (0.4 M pH adjusted to 9.0 with sodium hydroxide). D-Serine levels were then detected fluorometrically (344 nm excitation wavelength, 443 nm emission wavelength) by injecting 10 µl aliquots into the high-performance liquid chromatography system.

Compounds exemplary of those in this patent produced robust and significant increases in D-Serine levels in rat brain. In particular, a benzo[d]isoxazol-3-ol derivative administered in two separate doses (125 mg/kg followed by 75 mg/kg 3 hours later) produced a 2-fold increase in cerebellar D-Serine levels 6 hours after the first dose.

Example 8

Dosage Forms

Lactose-Free Tablet Dosage Form

Table 3 provides the ingredients for a lactose-free tablet dosage form of a compound of formula I and Ia:

TABLE 3

| Ingredient | Quantity per Tablet (mg) |
| --- | --- |
| 5-Chloro-benzo[d]isoxazol-3-ol | 75 |
| Microcrystalline cellulose | 125 |
| Talc | 5.0 |
| Water (per thousand tablets) | 30.0 mL* |
| Magnesium Stearate | 0.5 |

*The water evaporates during manufacture.

The active ingredient is blended with the cellulose until a uniform blend is formed. The smaller quantity of cornstarch is blended with a suitable quantity of water to form a corn starch paste. This is then mixed with the uniform blend until a uniform wet mass is formed. The remaining cornstarch is added to the resulting wet mass and mixed until uniform granules are obtained. The granules are then screened through a suitable milling machine, using a ¼ inch stainless steel screen. The milled granules are then dried in a suitable drying oven until the desired moisture content is obtained. The dried granules are then milled through a suitable milling machine using ¼ mesh stainless steel screen. The magnesium stearate is then blended and the resulting mixture is compressed into tablets of desired shape, thickness, hardness and disintegration. Tablets are coated by standard aqueous or nonaqueous technique.

Tablet Dosage Form

Another tablet dosage formulation suitable for use with the active ingredients of the invention is provided in Table 4.

TABLE 4

| | Quantity per Tablet (mg) | | |
| --- | --- | --- | --- |
| Ingredient | Formula A | Formula B | Formula C |
| 5-Chloro-benzo[d]isoxazol-3-ol | 20 | 40 | 100 |
| Microcrystalline cellulose | 134.5 | 114.5 | 309.0 |
| Starch BP | 30 | 30 | 60 |
| Pregelatinized Maize Starch BP | 15 | 15 | 30 |
| Magnesium Stearate | 0.5 | 0.5 | 1.0 |
| Compression Weight | 200 | 200 | 500 |

The active ingredient is sieved and blended with cellulose, starch and pregelatinized maize starch. Suitable volumes of purified water are added and the powders are granulated. After drying, the granules are screened and blended with the magnesium stearate. The granules are then compressed into tablets using punches.

Tablets of other strengths may be prepared by altering the ratio of active ingredient to pharmaceutically acceptable carrier, the compression weight, or by using different punches.

What is claimed is:

1. A compound of formula Ia or a pharmaceutically acceptable salt or solvate thereof:

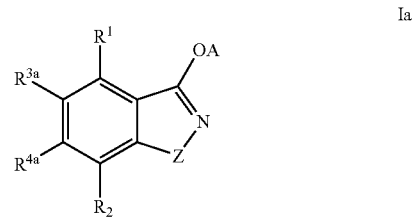

Ia wherein

A is hydrogen, alkyl or $M^+$;

M is aluminum, calcium, lithium, magnesium, potassium, sodium, zinc or a mixture thereof;

Z is O;

$R^1$ and $R^2$ are independently selected from hydrogen, alkyl, hydroxy, alkoxy, aryl, acyl, halo, cyano, haloalkyl, $NHCOOR^5$ and $SO_2NH_2$;

$R^5$ is aryl, arylalkyl, heteroaryl or heteroarylalkyl;

$R^{3a}$ and $R^{4a}$ are independently selected from alkyl, hydroxy, alkoxy, aryl, acyl, halo, cyano, haloalkyl, $NHCOOR^5$ and $SO_2NH_2$ with the proviso that not all of $R^1$, $R^2$, $R^{3a}$ and $R^{4a}$ are fluoro.

2. A compound according to claim 1, wherein $R^{3a}$ and $R^{4a}$ are independently selected from alkyl, hydroxy, alkoxy and halo.

3. A compound according to claim 1, wherein $R^{3a}$ and $R^{4a}$ are independently selected from alkyl and halo.

* * * * *